(12) United States Patent
Eull et al.

(10) Patent No.: US 8,617,199 B2
(45) Date of Patent: Dec. 31, 2013

(54) THIN FILM NASAL DILATOR WITH DELIVERY SYSTEM

(75) Inventors: Patricia A. Eull, Mahtomedi, MN (US); Matthew T. Scholz, Woodbury, MN (US); Kenneth A. Peterson, White Bear Lake, MN (US)

(73) Assignee: 3M Innovative Properties Company, Saint Paul, MN (US)

( * ) Notice: Subject to any disclaimer, the term of this patent is extended or adjusted under 35 U.S.C. 154(b) by 251 days.

(21) Appl. No.: 13/119,267

(22) PCT Filed: Sep. 30, 2009

(86) PCT No.: PCT/US2009/058939
§ 371 (c)(1),
(2), (4) Date: Mar. 16, 2011

(87) PCT Pub. No.: WO2010/039771
PCT Pub. Date: Apr. 8, 2010

(65) Prior Publication Data
US 2011/0166594 A1 Jul. 7, 2011

Related U.S. Application Data (60) Provisional application No. 61/101,600, filed on Sep. 30, 2008.

(51) Int. Cl.
*A61M 29/00* (2006.01)
(52) U.S. Cl.
USPC .......................................................... 606/199
(58) Field of Classification Search
USPC ..................................... 606/199; 128/200.24
See application file for complete search history.

(56) References Cited

U.S. PATENT DOCUMENTS

| | | |
|---|---|---|
| RE24,906 E | 12/1960 | Ulrich |
| 3,389,827 A | 6/1968 | Abere |
| 3,645,835 A | 2/1972 | Hodgson |
| 4,112,213 A | 9/1978 | Waldman |
| 4,310,509 A | 1/1982 | Berglund |
| 4,323,557 A | 4/1982 | Rosso |
| 4,472,480 A | 9/1984 | Olson |
| 4,737,410 A | 4/1988 | Kantner |
| 5,022,389 A | 6/1991 | Brennan |
| 5,088,483 A | 2/1992 | Heinecke |

(Continued)

FOREIGN PATENT DOCUMENTS

| | | |
|---|---|---|
| EP | 1033118 | 9/2000 |
| EP | 941723 | 2/2002 |

(Continued)

OTHER PUBLICATIONS

International Search Report for PCT/US2009/058939, 3 pages.

*Primary Examiner* — Gregory Anderson
(74) *Attorney, Agent, or Firm* — Trisha D. Adamson (57) ABSTRACT

The present invention discloses a nasal dilator comprising at least one breathable layer of adhesive-coated high MVTR layer, such as a polyurethane film, one or more adhesive-coated high modulus "spring" elements for dilating the nasal passages by applying a tension force to the skin, and a carrier delivery system. The carrier delivery system comprises a separation line or split through the carrier to allow for easy delivery of the nasal dilator. The carrier aids in the handling and delivery of the thin adhesive-coated high MVTR layer.

10 Claims, 4 Drawing Sheets

(56) References Cited

U.S. PATENT DOCUMENTS

| | | | |
|---|---|---|---|
| 5,160,315 A | 11/1992 | Heinecke | |
| 5,531,855 A | 7/1996 | Heinecke | |
| 5,533,499 A | 7/1996 | Johnson | |
| 5,533,503 A | 7/1996 | Doubek | |
| 5,614,310 A | 3/1997 | Delgado | |
| 5,653,224 A | 8/1997 | Johnson | |
| 5,669,377 A | 9/1997 | Fenn | |
| 5,738,642 A | 4/1998 | Heinecke | |
| 5,769,089 A | 6/1998 | Hand | |
| 5,842,469 A | 12/1998 | Rapp | |
| 5,849,325 A | 12/1998 | Heinecke | |
| 5,908,693 A | 6/1999 | Delgado | |
| 5,931,852 A | 8/1999 | Brennan | |
| 5,957,126 A | 9/1999 | Neeser | |
| 5,979,450 A | 11/1999 | Baker | |
| 6,090,403 A | 7/2000 | Block | |
| 6,098,616 A * | 8/2000 | Lundy et al. | 128/200.24 |
| 6,169,224 B1 | 1/2001 | Heinecke | |
| 6,206,902 B1 | 3/2001 | Morikane | |
| 6,264,976 B1 | 7/2001 | Heinecke | |
| 6,276,360 B1 | 8/2001 | Cronk | |
| 6,299,605 B1 | 10/2001 | Ishida | |
| 6,318,362 B1 | 11/2001 | Johnson | |
| 6,375,667 B1 | 4/2002 | Ruch | |
| 6,386,197 B1 | 5/2002 | Miller | |
| 6,461,467 B2 | 10/2002 | Blatchford | |
| 6,479,073 B1 | 11/2002 | Lucast | |
| 6,607,799 B1 | 8/2003 | Heinecke | |
| 6,685,682 B1 | 2/2004 | Peterson | |
| 6,971,388 B1 | 12/2005 | Michaels | |
| 7,114,495 B2 | 10/2006 | Lockwood | |
| 2001/0032645 A1 | 10/2001 | Cronk | |
| 2001/0056267 A1 | 12/2001 | Ishida | |
| 2005/0027230 A1 | 2/2005 | Beaudry | |
| 2005/0199245 A1 | 9/2005 | Brennan | |
| 2008/0058858 A1 | 3/2008 | Smith | |

FOREIGN PATENT DOCUMENTS

| | | |
|---|---|---|
| JP | 2000-197709 | 7/2000 |
| NL | 1010444 | 5/2000 |
| WO | WO 97-38651 | 10/1997 |
| WO | WO 98-15242 | 4/1998 |
| WO | WO 99-22678 | 5/1999 |
| WO | WO 99-27880 | 6/1999 |
| WO | WO 99-65430 | 12/1999 |
| WO | WO 01-60294 | 8/2001 |
| WO | WO 01-74432 | 10/2001 |
| WO | WO 03-090791 | 11/2003 |
| WO | WO 2006-099658 | 9/2006 |
| WO | WO 2007-056715 | 5/2007 |

* cited by examiner

THIN FILM NASAL DILATOR WITH DELIVERY SYSTEM

CROSS REFERENCE TO RELATED APPLICATIONS

This application is a national stage filing under 35 U.S.C. 371 of PCT/US2009/058939, filed Sep. 30, 2009, which claims priority to U.S. Provisional Application No. 61/101,600, filed Sep. 30, 2008, the disclosures of which is incorporated by reference in their entirety herein.

BACKGROUND

Nasal dilator products are currently sold in the consumer healthcare market today to alleviate a variety of breathing-related disorders. Nasal dilators typically function by attaching to the nose, and applying a force outward from the nasal region to hold open the nasal passages.

Types of nasal dilators include adhesive-coated breathable nonwovens and thick polyester strips as the material providing the spring force, and a polyolefin-type film in conjunction with polyester strips (spring material). These polyolefins have very low moisture vapor transmission rates (MVTR), which can lead to moisture build up under the nasal dilator, resulting in loss of adhesion and possibly discomfort (e.g., itchy feeling).

SUMMARY

In one embodiment, a nasal dilator is provided, comprising a breathable backing layer that comprises a first major surface and a second major surface; an adhesive layer on the first major surface of the breathable backing layer; a carrier releasably attached to the second major surface of the breathable backing layer, wherein the carrier is more rigid than the breathable backing layer and less rigid than the spring element; at least one spring element attached to the breathable backing layer on at least one of the first major surface or second major surface, wherein the spring element extends parallel to the longest side of the breathable backing layer and is coextensive with at least 75% of the length of the breathable backing layer; and a release liner.

In most embodiments, the spring element has sufficient spring force to return the spring element to its original position when not under stress and has a spring force that is less than the adhesive force of the adhesive layer to skin. In most embodiments, the spring element is attached to the adhesive on the first major surface of the backing.

In most embodiments, the nasal dilator further comprises a breathable facing layer proximate the first major surface of the breathable backing layer.

These and various other advantages and features characterizing the invention are pointed out with particularity in the claims annexed hereto and forming a part hereof. However, for a better understanding of the invention, its advantages, and objects obtained by its use, reference should be made to the accompanying drawings and descriptive matter, in which preferred embodiments of the invention are illustrated and described.

BRIEF DESCRIPTION OF THE DRAWINGS

The invention will be further described with reference to the drawings, wherein corresponding reference characters indicate corresponding parts throughout the several views, and wherein.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION OF PREFERRED EMBODIMENTS

The present invention discloses a nasal dilator comprising at least one breathable layer of adhesive-coated high MVTR layer, such as a polyurethane film, one or more adhesive-coated high modulus "spring" elements for dilating the nasal passages by applying a tension force to the skin, and a carrier delivery system. The carrier delivery system comprises a separation line or split through the carrier to allow for easy delivery of the nasal dilator. The carrier aids in the handling and delivery of the thin adhesive-coated high MVTR layer.

The high modulus spring elements are preferably made of thermoplastic polymers such as polyester. These spring elements can be adhered to either the top or bottom side of the polyurethane film to provide the spring force needed to open the nasal passages. The spring elements can also be sandwiched between two breathable layers as described below.

The spring elements are aligned generally parallel to the longest side of the breathable layer to aid in bridging the nasal passages (e.g., the nose). In most embodiments, the spring elements are substantially co-extensive with the length of the breathable layer(s). In most embodiments, the spring elements are co-extensive with at least 75% of the length of the breathable layer.

The adhesive-coated breathable layer is typically extremely thin, and generally very flexible. If the adhesive-coated breathable layer is not properly supported during application, it can easily fold over and adhere to itself, preventing proper application over the nasal surface. The adhesive-coated breathable layer is supported by a removable carrier attached to the top face of the backing layer. A release liner is also provided to contact the adhesive surface that will contact the patient during use. Both the release liner and conformable adhesive-coated breathable layer generally extend beyond the edges of the nasal spring elements.

Figure 1:
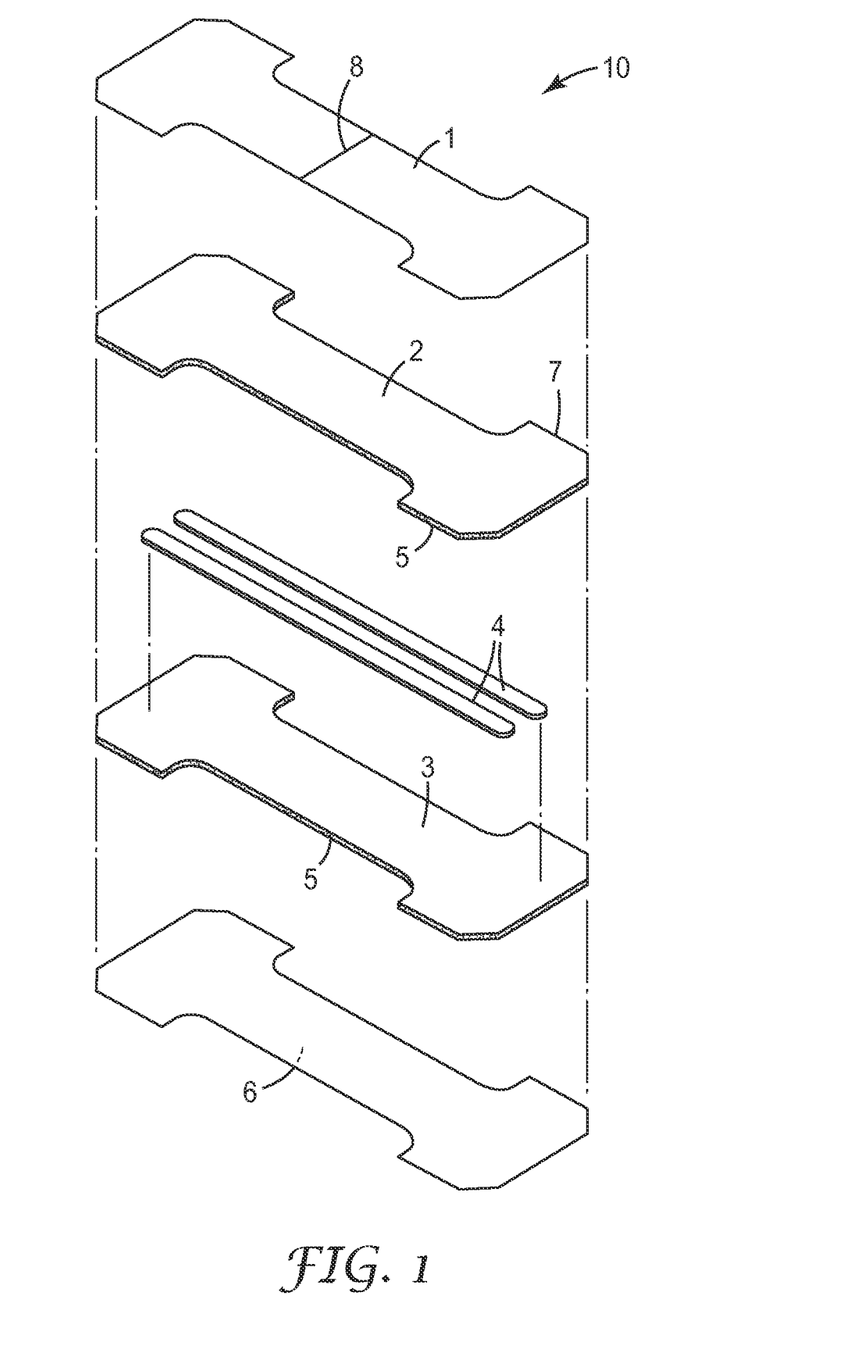
FIG. 1 is an exploded perspective view of an exemplary embodiment of the present invention.
Figure 2:
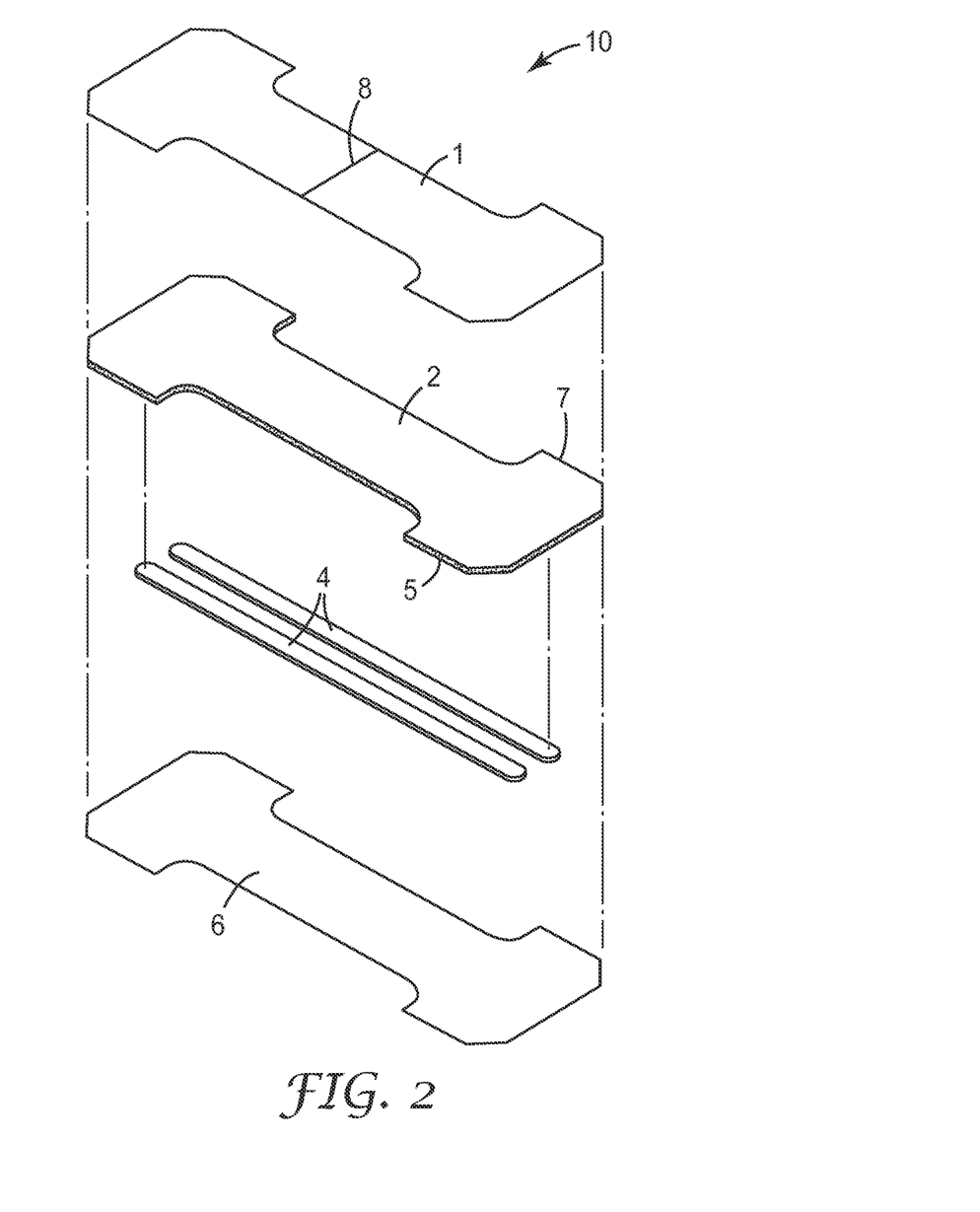
FIG. 2 is an exploded perspective view of another exemplary embodiment of the present invention.

FIGS. 1-2 depict exemplary embodiments of the nasal dilator and delivery system designated in its entirety by the reference numeral 10. FIG. 1 depicts nasal dilator 10 with nasal spring elements 4 between breathable backing layer 2 (coated with adhesive 5) and breathable facing layer 3 (coated with adhesive 5). The adhesive 5 coated on the breathable backing layer 2 can be the same or different than the adhesive 5 coated on breathable facing layer 3.

Figure 3A:
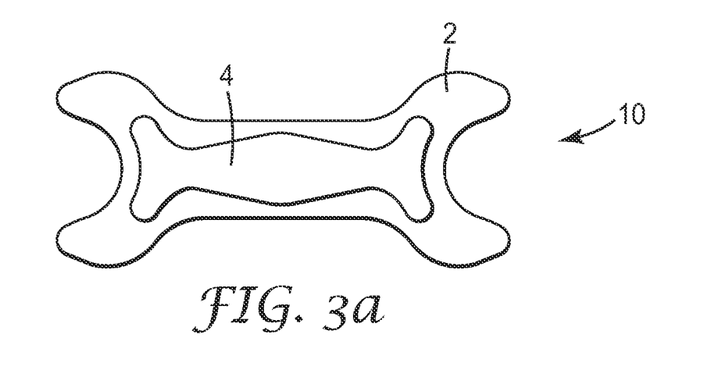
FIG. 3a is a bottom plan view of an exemplary embodiment of the present invention.
Figure 3B:
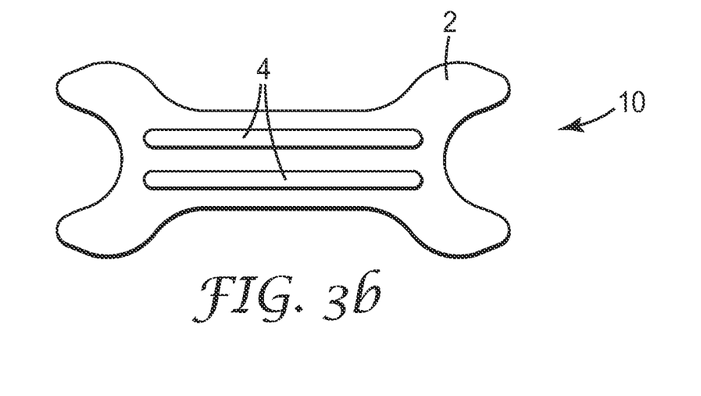
FIG. 3b is a bottom plan view of another exemplary embodiment of the present invention.
Figure 3C:
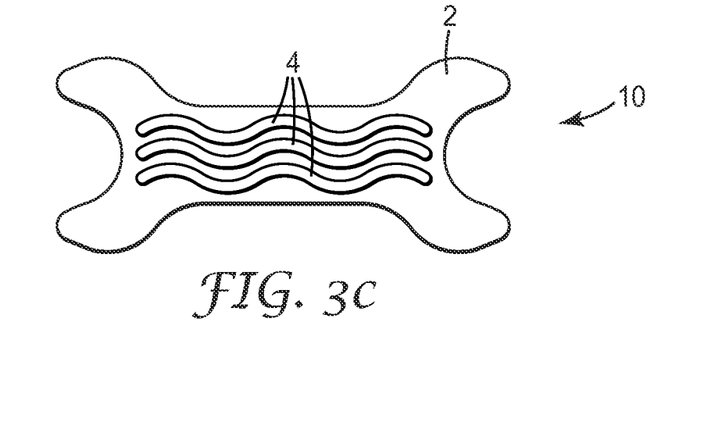
FIG. 3c is a bottom plan view of another exemplary embodiment of the present invention.

The nasal spring elements 4 are generally parallel to the length of nasal dilator 10. Nasal spring elements 4 are also generally co-extensive with the length of nasal dilator 10 as well. In most embodiments, the nasal spring elements 4 are co-extensive with at least 75% of the length of nasal dilator 10 on its longest side. Although nasal spring elements 4 are shown as two narrow strips parallel and co-extensive with the length of the nasal dilator 10 as shown in FIGS. 1-2 (and FIG. 3b) the nasal spring elements 4 can take any appropriate shape, comprise a single nasal spring element 4 as shown in FIG. 3a, or comprise multiple nasal spring elements 4 as shown in FIGS. 3b and 3c, and/or can be located off-center on the nasal dilator 10 as desired.

In FIG. 1, the nasal spring elements 4 are affixed by an adhesive 5 on the breathable backing layer 2 that extends out to the perimeter 7 of the dilator 10. The breathable backing layer 2 is typically extremely thin, flexible, and either transparent or translucent, allowing the nasal spring elements 4 to be viewed through it, if desired.

In FIG. 1, an optional breathable facing layer 3 is affixed to the nasal spring elements 4 and the breathable backing layer 2 (coated with adhesive 5). The breathable facing layer 3 is also coated with an adhesive 5 on the bottom face of the breathable facing layer such that the adhesive 5 contacts the patient when the nasal dilator 10 is applied. Breathable backing layer 2 and breathable facing layer 3 can be the same or different materials, although preferably both layers are breathable materials as described further below.

A release liner 6 covers the adhesive 5 coated on the bottom face of the breathable facing layer 3, and typically remains attached to dilator 10 until a user is ready to apply the dilator 10. Release liner 6 may optionally extend beyond the adhesive coated face of breathable facing layer 3 (not shown) to enable easy removal by the user. The release liner 6 may be a single piece or multiple piece release liner, and may be part of or laminated to the package (not shown) containing the nasal dilator, or merely enclosed along with the nasal dilator within the package.

A carrier layer 1 is positioned over the breathable backing layer 2. The carrier layer 1 can be a single piece of material or can be two or more distinct pieces. The carrier layer 1 is substantially co-extensive with breathable backing layer 2 with the breathable backing layer 2 sandwiched between the carrier layer 1 and nasal spring elements 4. As used herein, the term "sandwiched" means that one layer is intermediate or between two other layers.

In preferred embodiments, as shown in FIGS. 1 and 2, a separation line 8 may be provided in carrier layer 1. The separation line 8 allows for easy removal of the carrier layer 1 after application by the user, see also FIG. 4.

Pressure sensitive adhesive layer 5 is generally provided on one major surface of the breathable backing layer 2 in order to make it adhesive, and a low adhesion coating (low adhesion backsize or LAB) may be provided on the other major surface of the breathable backing layer 2 on the side that comes in contact with the carrier layer 1. The low adhesion coating reduces the need to change the dilator 10 due to unwanted dilator removal when other devices or a user's fingers contact the nasal dilator during use, and also reduces the surface friction of the dilator 10 against other materials such as clothing, thereby offering additional protection against the accidental removal of dilator 10. A description of a low adhesion backing material suitable for use with the present invention can be found in U.S. Pat. Nos. 5,531,855 and 6,264,976, which are compatible with a heat seal bond described below, and are incorporated herein in their entirety.

The carrier layer 1 is preferably attached to the second major surface of the breathable backing layer 2 (over the low adhesion backing) The bond between the carrier layer 1 and the breathable backing layer 2 is usually stronger than the bond between the adhesive layer 5 and the release liner 6 so that the breathable backing layer 2 remains attached to the carrier layer 1 when the release liner 6 is removed from the dilator 10. Once the release liner 6 and dilator 10 are separated, only the carrier layer 1 and nasal spring elements 4 provide significant rigidity to the breathable backing layer 2.

Various other embodiments are contemplated from the aspects shown in FIGS. 1-2. For example, the breathable backing layer 2 can be multiple films or coatings without diverging from the invention or deviating from the meaning of the term "film" as used herein. Similarly, the nasal spring elements 4 can include multiple sub-layers, including films, webs, sheets, etc. Also, additional layers and films of other materials can be added between the materials described herein.

The nasal spring elements 4 can comprise the materials described further below to provide sufficient rigidity and elastic recovery to allow the nasal spring element to apply a tension force that opens the nasal passages without separating from or ripping the breathable backing layer 2. In most embodiments, the nasal spring elements 4 comprise a material with sufficient spring force to pull apart and open the nasal passages when placed against the nasal passages in a stressed position, and sufficient spring force to return the nasal spring elements 4 to its original unstressed position when the stress is removed, but otherwise having a spring force when stressed that is less than the adhesive force that retains the nasal dilator 10 on the skin.

In some embodiments, the nasal spring elements 4 have a thickness of at least 51 micrometers (2 mils). The breathable backing layer 2 can comprise a transparent elastic polymeric film (e.g., urethane) having a thickness in the range of 0.02 to 0.2 mm and most preferably 0.021-0.051 mm.

In an alternate exemplary embodiment as shown in FIG. 2, the nasal spring elements 4 can be located between the breathable backing layer 2 and the release liner 6, without the presence of a breathable facing layer. The nasal spring elements 4 will preferably have a pressure sensitive adhesive (not shown) coated on the surface of the nasal spring element 4 that faces the release liner 6.

In alternate exemplary embodiments (not shown) the nasal spring elements 4 can be sandwiched between the breathable backing layer 2 and adhesive 5, or between breathable backing layer 2 and carrier layer 1. These embodiments may be less preferred due to aesthetic reasons. In those embodiments that include the nasal spring elements 4 located between the breathable backing layer 2 and the carrier layer 1, the carrier layer 1 may have to be affixed by adhesive rather than heat-sealed bonded to the breathable backing layer 2.

Regardless of its location, it is preferred that the nasal spring elements 4 be firmly attached to the breathable backing layer 2 such that nasal spring elements 4 do not delaminate from the breathable backing layer 2.

FIGS. 3a-3c show alternate exemplary embodiments of the nasal dilator 10 with the release liner 6 removed. Nasal spring elements 4 can be a single or multiple strips of material. The breathable backing layer 2 can also be in any shape that is conformable and wearable by a user on the nasal passages. The nasal spring elements 4 can also vary in shape and size (e.g., straight, sinusoidal or wavy) provided they are substantially co-extensive with the length of the breathable layer(s).

Figure 4:
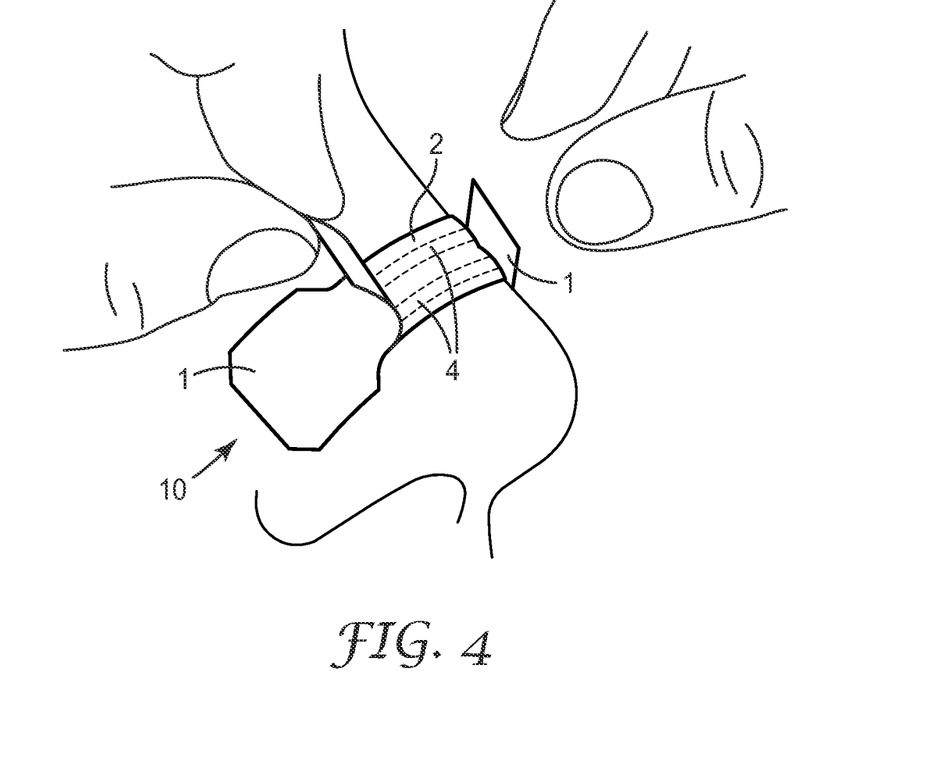
FIG. 4 is an exemplary depiction of a method of applying and removing the nasal dilator of FIG. 1 or 2 to a patient.

FIG. 4 depicts an exemplary method of applying the dilator 10 of FIGS. 1-2 to a patient. The dilator 10 is typically applied to a patient by first optionally cleaning the application area. The release liner 6 (not shown) is then removed from the dilator, exposing the bottom face of the breathable facing layer 3 coated with adhesive 5 (according to FIG. 1) or the nasal spring elements 4 and breathable backing layer coated with adhesive 5 (according to FIG. 2). Once removed from release liner 6, breathable facing layer 3 (according to FIG. 1) or the nasal spring elements 4 (according to FIG. 2) is brought in contact with the skin covering the nasal passages, and then the edges of the dilator 10 are gently and smoothly pressed against the patient, thereby bringing the exposed adhesive 5 in contact with the patient.

After the dilator 10 is properly in position and adhered to a patient's skin, the carrier layer 1 can be removed, as shown in FIG. 4. Generally removal of carrier layer 1 is accomplished by grasping the carrier layer at separation line 8, which can separate the carrier into two separate pieces on application of nasal dilator 10 over the bridge of the patient's nose. A peeling motion toward the edges of the dilator 10 effectively removes the carrier layer 1.

The layers and materials discussed above are further described in detail below.

Breathable Backing and Facing Layer Materials

Suitable materials for breathable backing layer 2, and optional breathable facing layer 3 when used, typically include translucent or transparent polymeric elastic films. The backing can be a high moisture vapor permeable film backing U.S. Pat. No. 3,645,835 describes methods of making such films and methods for testing their permeability.

The breathable backing layer advantageously should transmit moisture vapor at a rate equal to or greater than human skin. In some embodiments, the adhesive coated backing layer transmits moisture vapor at a rate of at least 300 g/m$^2$/24 hrs/37° C./100-10% RH, frequently at least 700 g/m$^2$/24 hrs/37° C./100-10% RH, and most typically at least 2000 g/m$^2$/24 hrs/37° C./100-10% RH using the inverted cup method.

The backing film preferably has an MVTR of at least 600, preferably at least 800 and post preferably at least 1000 g/M2/24 hr when tested according to the inverted cup method described in U.S. Pat. No. 5,979,450. Suitable backing materials include polyurethanes such as polyester or polyether polyurethanes (e.g., "Estane™ thermoplastic polyurethane," commercially available from B.F. Goodrich, Cleveland Ohio), polyesters such as polyether polyester (e.g., "Hytrel™ polyester elastomer," commercially available from Du Pont Co., Wilmington, Del.), and polyamides such as polyether polyamides (e.g., "Pebax™ Resins" commercially available from ELF Atochem, North America, Inc., Philadelphia, Pa.).

The breathable backing layer 2, and optional breathable facing layer 3 when used, is generally conformable to anatomical surfaces. As such, when the breathable backing layer 2 is applied to an anatomical surface, it conforms to the surface even when the surface moves. A description of breathable backing layers 2 and breathable facing layers 3 for use with the present invention can be found in U.S. Pat. Nos. 5,088,483 and 5,160,315. Specific suitable backing materials are elastomeric polyurethane, co-polyester, or polyether block amide films. These films combine the desirable properties of resiliency, high moisture vapor permeability, and transparency found in backings Carrier Layer The material used to form the carrier layer 1 is generally substantially more rigid than the breathable backing layer 2 to prevent the breathable backing layer 2 from improperly wrinkling during application to a patient. The carrier layer 1 can be heat-sealable to the breathable backing layer 2 with or without a low adhesion coating described in general. In general, the carrier layer materials can include, but are not limited to, polyethylene/vinyl acetate copolymer-coated papers and polyester films. One example of a suitable carrier layer material is a polyethylene/vinyl acetate copolymer coated super calendared Kraft paper (1-80BKG-157 PE; LOPAREX of Willowbrook, Ill.).

The carrier layer 1 can include a separation line 8 to aid in separating portions of the carrier layer 1 after application of the dilator 10 on a patient. Spacing and shape of the separation lines are adjusted to give a carrier layer with relatively easy separation on application of the nasal dilator to the bridge of the nose. The separation line may be shaped in any desirable configuration including linear, angled, Y-shaped, V-shaped, sinusoidal, etc.

Adhesive Layer

Various pressure sensitive adhesives can be used to form adhesive layer 5 on the breathable backing layer 2, nasal spring elements 4, and/or optional breathable facing layer 3 to make any one of the layers adhesive. The pressure sensitive adhesive is usually reasonably skin compatible and "hypoallergenic", such as the acrylate copolymers described in U.S. Pat. No. RE 24,906. Particularly useful is a 97:3 iso-octyl acrylate: acrylamide copolymer, as is a 70:15:15 isooctyl acrylate: ethyleneoxide acrylate: acrylic acid terpolymer which is described in U.S. Pat. No. 4,737,410. Additional useful adhesives are described in U.S. Pat. Nos. 3,389,827, 4,112,213, 4,310,509, and 4,323,557. Inclusion of medicaments or antimicrobial agents in the adhesive is also contemplated, as described in U.S. Pat. Nos. 4,310,509 and 4,323,557.

The adhesive layer 5 can be coated on the breathable backing layer 2, nasal spring elements 4, and/or optional breathable facing layer 3 by a variety of processes, including, direct coating, lamination, and hot lamination, Release Liner Release liner 6 suitable for use as described herein can be made of kraft papers, polyethylene, polypropylene, polyester or composites of any of these materials. The films are preferably coated with release agents such as fluorochemicals or silicones. For example, U.S. Pat. No. 4,472,480 describes low surface energy perfluorochemical liners. The liners are papers, polyolefin films, or polyester films coated with silicone release materials. Examples of commercially available silicone coated release papers are POLYSLIK™, silicone release papers available from Rexam Release (Bedford Park, Ill.) and silicone release papers supplied by LOPAREX (Willowbrook, Ill.). Other non-limiting examples of such release liners commercially available include siliconized polyethylene terephthalate films commercially available from H. P. Smith Co. and fluoropolymer coated polyester films commercially available from 3M Company under the brand "ScotchPak™" release liners.

Nasal Spring Element

The nasal spring elements provide a spring force when the nasal dilator is bent around and adhered to the external part of the nose. This spring force causes the nostrils to open or dilate. Suitable nasal spring element materials include high modulus thermoplastics such as polyesters (e.g., PET, PLA, etc.), acrylics, polyamides, etc. Also suitable are thermoset polymers such as acrylics, polyesters, epoxies and the like. In some cases metallic strips are suitable as well.

The high modulus materials typically used in embodiments of the present invention have a modulus of at least 200 kpsi, more preferably at least 300 kpsi, and even more preferably at least 400 kpsi, as measured by ASTM D822. In a preferred embodiment, the modulus of the film, such as those used in the Examples below, is approximately 500 kpsi (measured using ASTM D822). Typically the materials have some degree of crystallinity to aid in rigidity and spring force characteristics.

EXAMPLES

Example 1

Step 1

A 0.8 mil (20 micron) film of "Estane 58309NAT022" polyurethane resin (B.F. Goodrich, Cleveland, Ohio) was extruded onto a poly-coated paper carrier (polyethylene/vinyl acetate copolymer coated super calendared Kraft paper (Wausa Paper, Rhinelander, Wis.). The conditions of the extrusion process were set to achieve a uniform bond between paper and film so that this bond is maintained through further processing but will separate easily when used in the final product configuration. The target Film/Paper bond strength had a 90 degree peel value between 8-50 grams/inch (3-20 grams/cm)

Step 2

Twenty-five grams per square meter of an adhesive prepared in accordance with U.S. Pat. No. RE 24,906, comprising a 97:3 units of iso-octyl acrylate: acrylamide copolymer was laminated onto the film side of the film/paper laminate described in Step 1 above and wound into roll form with the adhesive side facing inward. The resultant adhesive-coated polyurethane film with heat laminated carrier was then cut into sheets measuring 4×6 inches (10×15 cm).

Step 3

The adhesive-coated polyester spring material was prepared in the following manner. A tackified 96:4 iso-octylacrylate/acrylic acid adhesive (3M Company, Cordova, Ill.) was extruding at a thickness of 1.2 mils (30.5 microns) onto a 63 lb. (139 Kg) poly-coated kraft paper (Loparex, Willowbrook, Ill.). Then a 10 mil (254 micron) polyester film (DuPont-Teijin, Chester, Va.) was laminated to the adhesive side and wound into roll form. The resultant adhesive-coated polyester was slit to 0.125 inch (3.2 mm) width strips of spring material.

Step 4

Two strips of adhesive-coated polyester spring material prepared in Step 3 measuring 0.125 inch (3.2 mm) by 6 inch (15 cm) were adhered to the adhesive side of the 4 inch by 6 inch sheet of adhesive-coated polyurethane with paper carrier prepared in Step 2. The two strips of spring material were oriented in parallel down the center of the sheet with a 0.06 inch (1.5 mm) gap between strips. The adhesive-coated polyester was laminated so that the top side of the polyester film was adhered to the adhesive side of the polyurethane film.

Step 5

Twenty-five grams per square meter of an adhesive prepared in accordance with U.S. Pat. No. 24,906, comprising a 97:3 units of iso-octyl acrylate: acrylamide copolymer was applied to a release liner of 78 pounds per ream (127 grams per meter squared) bleached, one-side coated, polyethylene and silicone paper (Rhinelander, Wis.)) utilizing a standard horizontal knife coater. A 0.8 mil (20 micron) film of "Estane 58309NAT022" polyurethane resin (B.F. Goodrich, Cleveland, Ohio) was laminated to the adhesive surface. The resultant tape was wound into roll form and then cut into 4 inch by 6 inch sheets.

Step 6

The laminate construction of Step 4 was adhered to the top side of the adhesive-coated 0.8-mil polyurethane film with liner prepared in Step 5. This multilayer construction was die cut into the desired shape.

Step 7

The top carrier release liner (paper directly in contact with the polyurethane film) was cut across the width, directly in the center of the strip being careful not to cut into the film surface directly underneath it.

Example 2

Steps 1 to 4 were performed the same as Steps 1 to 3 of Example 1.

Step 5

The laminate construction of Step 4 was adhered to a release liner of 78 pounds per ream (127 grams per meter squared) bleached, one-side coated, polyethylene and silicone paper (Rhinelander, Wis.)). This multilayer construction was die cut into the desired shape, shown in FIG. 1.

Step 6

The top carrier release liner (paper directly in contact with the polyurethane film) was cut across the width, directly in the center of the strip being careful not to cut into the film surface directly underneath it.

As various changes could be made in the above constructions, compositions and methods without departing from the scope of the invention as defined in the claims, it is intended that all matter contained in the above description or shown in the accompanying drawings be interpreted as illustrative and not in a limiting sense. The Examples described in this application are illustrative of the possibilities of varying the type, quantity and ratio of composition as well as the methods for making formulations of the present invention. The complete disclosures of all patents, patent applications, and publications recited herein are incorporated by reference, as if individually incorporated by reference.

What is claimed is:

1. A nasal dilator, comprising
   a breathable backing layer that comprises a first major surface and a second major surface;
   an adhesive layer on the first major surface of the breathable backing layer;
   a carrier releasably attached to the second major surface of the breathable backing layer, wherein the carrier is more rigid that the breathable backing layer and less rigid than the spring element;
   at least one spring element attached to the breathable backing layer on at least one of the first major surface or second major surface, wherein the spring element extends parallel to the longest side of the breathable backing layer and is coextensive with at least 75% of the length of the breathable backing layer; and
   a release liner.

2. The nasal dilator of claim 1, wherein the spring element has sufficient spring force to return the spring element to its original position with the removal of stress and wherein the spring force is less than the adhesive force of the adhesive layer to skin.

3. The nasal dilator of claim 1, wherein the spring element is attached to the adhesive on the first major surface of the backing.

4. The nasal dilator of claim 1, further comprising a breathable facing layer proximate the first major surface of the breathable backing layer.

5. The nasal dilator of claim 1, wherein the spring element comprises a high modulus thermoplastic material.

6. A method of dilating the nasal passages, comprising:
   providing the nasal dilator of claim 1,
   removing the release liner,
   adhering the breathable layer to the patient, and
   removing the carrier layer,
   wherein the spring element applies force to the skin of the nose to open the nasal passages while the breathable layer remains adhered to the skin.

7. The nasal dilator of claim 1, wherein the breathable backing layer comprises a high moisture vapor permeable film backing.

8. The nasal dilator of claim 7, wherein the breathable backing layer transmits moisture vapor at a rate of at least 300 g/m$^2$/24 hrs/37° C./100-10% RH.

9. The nasal dilator of claim 7, wherein the breathable backing layer transmits moisture vapor at a rate of at least 700 g/m$^2$/24 hrs/37° C./100-10% RH.

10. The nasal dilator of claim 7, wherein the breathable backing layer transmits moisture vapor at a rate of at least 2000 g/m$^2$/24 hrs/37° C./100-10% RH.

* * * * *

UNITED STATES PATENT AND TRADEMARK OFFICE
CERTIFICATE OF CORRECTION

PATENT NO.        : 8,617,199 B2
APPLICATION NO.   : 13/119267
DATED             : December 31, 2013
INVENTOR(S)       : Patricia Eull Page 1 of 1

It is certified that error appears in the above-identified patent and that said Letters Patent is hereby corrected as shown below:

In the Specification

Column 3
Line 67             Delete "backing)" and insert -- backing). --, therefor.

Column 5
Line 25             Delete "backing" and insert -- backing. --, therefor.
Line 35             Delete "1000 g/M2/" and insert -- 1000 g/m$^2$/ --, therefor.
Line 57             Delete "backings" and insert -- backings. --, therefor.

Column 6
Line 31             Delete "lamination," and insert -- lamination. --, therefor.

Column 7
Line 10             Delete "(Wausa Paper," and insert -- (Wausau Paper, --, therefor.
Line 16             Delete "grams/cm)" and insert -- grams/cm). --, therefor.
Line 52             Delete "Wis.))" and insert -- Wis.) --, therefor.

Column 8
Line 9 (Approx.)    Delete "Wis.))." and insert -- Wis.). --, therefor.

In the Claims

Column 8
Line 38             In Claim 1, delete "that" and insert -- than --, therefor.

Signed and Sealed this
Eleventh Day of November, 2014

Michelle K. Lee
*Deputy Director of the United States Patent and Trademark Office*